United States Patent
Armstrong et al.

(10) Patent No.: US 10,053,610 B2
(45) Date of Patent: Aug. 21, 2018

(54) ANTIFREEZE PROTEINS FOR USE IN DOWNHOLE FLUIDS

(71) Applicant: BAKER HUGHES INCORPORATED, Houston, TX (US)

(72) Inventors: Charles David Armstrong, Tomball, TX (US); Qi Qu, Spring, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 0 days.

(21) Appl. No.: 15/463,490

(22) Filed: Mar. 20, 2017

(65) Prior Publication Data

US 2017/0204317 A1 Jul. 20, 2017

Related U.S. Application Data

(62) Division of application No. 14/674,634, filed on Mar. 31, 2015, now Pat. No. 9,624,418.

(60) Provisional application No. 61/979,847, filed on Apr. 15, 2014.

(51) Int. Cl.
C09K 8/035 (2006.01)
C09K 8/62 (2006.01)
C09K 5/20 (2006.01)
C07K 14/195 (2006.01)

(52) U.S. Cl.
CPC ............ C09K 8/035 (2013.01); C07K 14/195 (2013.01); C09K 5/20 (2013.01); C09K 8/62 (2013.01); C09K 2208/22 (2013.01)

(58) Field of Classification Search
None
See application file for complete search history.

(56) References Cited

U.S. PATENT DOCUMENTS

| | | | |
|---|---|---|---|
| 5,460,728 A | * | 10/1995 | Klomp ............... C09K 8/52 210/698 |
| 6,444,852 B1 | | 9/2002 | Milburn et al. |
| 6,914,043 B1 | | 7/2005 | Chapman et al. |
| 2005/0161631 A1 | | 7/2005 | Walker et al. |
| 2015/0161631 A1 | | 7/2005 | Walker |
| 2012/0005783 A1 | | 1/2012 | Spangenberg et al. |
| 2014/0256599 A1 | | 9/2014 | Kelland |
| 2015/0260348 A1 | | 9/2015 | Talley et al. |

FOREIGN PATENT DOCUMENTS

| | | | |
|---|---|---|---|
| CA | 2496631 A1 | * 10/2003 | ............... C10L 3/06 |
| WO | 2013050773 | 4/2013 | |

OTHER PUBLICATIONS

Garnham CP, et al., Anchored clathrate waters bind antifreeze proteins to ice, PNAS 108(18); 2011; 7363-7367.

(Continued)

*Primary Examiner* — John J Figueroa
(74) *Attorney, Agent, or Firm* — Mossman, Kumar & Tyler, P.C.

(57) ABSTRACT

Antifreeze proteins having an ice-binding site, such as those derived from the *Marinomonas primoryensis* bacterium, may be used in additive compositions, fluid compositions, and methods for depressing the freezing point of the fluid compositions. The fluid composition may include the antifreeze protein and a base fluid, such as drilling fluids, servicing fluids, production fluids, completion fluids, injection fluids, refinery fluids, and combinations thereof.

9 Claims, 2 Drawing Sheets

```
HMNVSQSNSFGFWDGTSTQAEITHSFDHYIGSAFDASNNNVAVTGNVSATLNV
LAGDDKVSIDGNVEDVLVAANVAVLDMGTGNDQLYVAGDVLGKIDAGTGNDEI
YIKGDVSAAVDAGTGNDEVYIGGNLSGDLDAGTDNDNIQIGGDVNAALNAGTG
NDNLIIGHDVSGIVNMGTDNDTVEVGRTINASGKVLLDTGDDSLLVSGDLFGE
VDGGTGNDTIIIAGKVSGNIQGGTGNDIVRVQSQVWAEANISLGTGDDVLIVE
HELHGTVAGNEGDDSIYLKFYTKEQYNNSDLRNRVANFEHIRVSDGVVKGSP
ADFADYAAGHNHNHNHNHN*GS
```

(56) References Cited

OTHER PUBLICATIONS

NCBI, GenBank Accession No. ABL74378.1; Dec. 2006.
Garnham, Christopher P., et al., "A Ca2+-dependent bacterial antifreeze protien domain has a novel beta-helical ice-binding fold," Biochemical Journal, 2008, vol. 411, No. 1, 171-180.

\* cited by examiner

5'
CATATGAACGTCTCGCAGAGCAACAGCTTTGGCTTTTGGGATGGCACCAGCA
CGCAGGCAGAAATCACGCATTCCTTTGACCACTACATTGGCAGTGCGTTTGAT
GCCTCCAACAATAACGTGGCTGTTACCGGTAACGTGAGCGCAACGCTGAATG
TTCTGGCTGGCGATGACAAAGTCTCTATCGATGGTAACGTGGAAGACGTCCT
GGTGGCGGCCAATGTTGCAGTCCTGGATATGGGCACCGGTAACGACCAGCTG
TATGTGGCGGGCGATGTTCTGGGTAAAATCGACGCCGGCACGGGTAATGATG
AAATCTACATTAAGGGCGACGTCTCAGCAGCTGTGGATGCAGGCACCGGTAA
CGACGAAGTGTATATTGGCGGTAATCTGTCGGGCGATCTGGACGCTGGTACG
GATAACGACAATATCCAAATTGGCGGTGATGTTAACGCGGCCCTGAATGCGG
GCACCGGTAACGATAATCTGATTATCGGCCATGATGTTAGCGGTATCGTCAA
CATGGGCACCGATAATGACACGGTGGAAGTTGGTCGTACCATTAACGCCTCT
GGCAAAGTGCTGCTGGATACGGGTGATGACAGCCTGCTGGTTTCTGGCGACC
TGTTTGGTGAAGTCGACGGCGGTACCGGCAATGATACGATTATCATTGCGGG
CAAGGTGAGCGGTAACATCCAGGGCGGTACCGGTAATGATATTGTCCGCGTG
CAGTCACAAGTTTGGGCAGAAGCTAACATCTCGCTGGGCACCGGTGATGACG
TTCTGATTGTCGAACATGAACTGCACGGTACGGTGGCCGGCAATGAAGGTGA
TGACAGTATCTACCTGAAGTTCTACACCAAGGAACAATACAACAACAATTCC
GATCTGCGTAACCGCGTTGCAAATTTCGAACACATTCGCGTCTCAGATGGCGT
GGTCAAGGGCTCCCCGGCGGACTTTGCGGACTACGCTGCAGGTCATAATCAT
AATCATAATCATAATCATAATCACAATTAAGGATCC--3'

FIG. 1A

HMNVSQSNSFGFWDGTSTQAEITHSFDHYIGSAFDASNNNVAVTGNVSATLNV
LAGDDKVSIDGNVEDVLVAANVAVLDMGTGNDQLYVAGDVLGKIDAGTGNDEI
YIKGDVSAAVDAGTGNDEVYIGGNLSGDLDAGTDNDNIQIGGDVNAALNAGTG
NDNLIIGHDVSGIVNMGTDNDTVEVGRTINASGKVLLDTGDDSLLVSGDLFGE
VDGGTGNDTIIIAGKVSGNIQGGTGNDIVRVQSQVWAEANISLGTGDDVLIVE
HELHGTVAGNEGDDSIYLKFYTKEQYNNNSDLRNRVANFEHIRVSDGVVKGSP
ADFADYAAGHNHNHNHNHNHN*GS

ANTIFREEZE PROTEINS FOR USE IN DOWNHOLE FLUIDS

CROSS-REFERENCE TO RELATED APPLICATION

This application is a divisional application of U.S. patent application Ser. No. 14/674,634 filed Mar. 31, 2015, issued as U.S. Pat. No. 9,624,418 on Apr. 18, 2017, and this application further claims the benefit of Provisional Patent Application No. 61/979,847 filed Apr. 15, 2014, all of which are incorporated by reference herein in their entirety.

TECHNICAL FIELD

The present invention relates to additive compositions, fluid compositions, and methods for using at least one antifreeze protein in a downhole fluid, and more specifically relates to depressing the freezing point of the fluid compositions with an antifreeze protein, such as those derived from *Marinomonas primoryensis*.

BACKGROUND

A number of hydrocarbons, especially lower-boiling light hydrocarbons in formation fluids or natural gas are known to form hydrates in conjunction with water present under a variety of conditions—particularly at the combination of lower temperature and higher pressure. The hydrates usually exist in solid forms that are essentially insoluble in the fluid itself. The solid hydrates may cause issues for production, handling, and transport of these fluids. For example, hydrate solids (or crystals) may cause plugging and/or blockage of pipelines, transfer lines, other conduits, valves, safety devices, and/or other equipment, which may result in shut-down, loss of production, risk of explosion, or unintended release of hydrocarbons into the environment either on-land or off-shore.

Hydrocarbon hydrates are clathrates, which are cage structures formed between a host molecule and a guest molecule. A hydrocarbon hydrate may be composed of crystals formed by water host molecules surrounding the hydrocarbon guest molecules. The smaller or lower-boiling hydrocarbon molecules, particularly $C_1$ (methane) to $C_4$ hydrocarbons and their mixtures, may be more problematic because their hydrate or clathrate crystals may be easier to form.

The guest molecules trapped in hydrates typically may be hydrocarbon gases, such as methane, ethane, propane, butane and isobutane. Alkenes, alkynes, methyl substituted butanes and pentanes, cyclic alkanes from cyclopropane to cyclooctane, cycloalkenes and their methyl-substituted analogs may also be present as guest molecules. Other possible guests in natural hydrates are small molecules, such as $CO_2$, $H_2S$, the noble gases (Ar, Kr, Xe), oxygen and nitrogen. Such clathrate hydrates can also be formed in laboratory and industrial settings as well as clathrate hydrates formed by ethers, ketones, aldehydes, mercaptans, sulfides, halogenated hydrocarbons, and a number of inorganic molecules including, but not limited to, $SF_6$, $PH_3$, $H_2Se$, $SO_2$, $ClO_2$, CO, $ClO_3F$, $SO_2F_2$, $NF_3$, $Cl_2$, $Br_2$, and COS. Even certain non-hydrocarbons, such as carbon dioxide, nitrogen and hydrogen sulfide are known to form hydrates under certain conditions.

Thermodynamic and kinetic techniques may be used to overcome or control the hydrocarbon hydrate problems. For the thermodynamic approach, there are a number of reported or attempted methods, including water removal, increasing temperature, decreasing pressure, addition of "antifreeze" additives to the fluid and the like. The kinetic approach generally attempts (a) to prevent the smaller hydrocarbon hydrate crystals from agglomerating into larger ones and/or (b) to inhibit and/or retard initial hydrocarbon hydrate crystal nucleation; and/or crystal growth.

Another problem in oil drilling and exploration involves the formation of scale. Scale is a deposit or coating formed on the surface of metal, rock or other materials. Scale formation may be caused by a precipitation from a chemical reaction with the surface, precipitation caused by chemical reactions, a change in pressure or temperature, or a change in the composition of a solution. Typical scales are calcium carbonate, calcium sulfate, barium sulfate, strontium sulfate, iron sulfide, iron oxides, iron carbonate, various silicates and phosphates and oxides, or any of a number of compounds insoluble or slightly soluble in water.

Hydrate and/or scale formation are deleterious in many downhole fluids, such as drilling fluids, completion fluids, servicing fluids (e.g. fracturing fluids), production fluids, injection fluids, and combinations thereof. Drilling fluids are typically classified according to their base fluid. In water-based fluids, solid particles, such as weighting agents, are suspended in a continuous phase consisting of water or brine. Oil can be emulsified in the water, which is the continuous phase. "Water-based fluid" is used herein to include fluids having an aqueous continuous phase where the aqueous continuous phase can be all water or brine, an oil-in-water emulsion, or an oil-in-brine emulsion. Brine-based fluids, of course are water-based fluids, in which the aqueous component is brine.

Oil-based fluids are the opposite or inverse of water-based fluids. "Oil-based fluid" is used herein to include fluids having a non-aqueous continuous phase where the non-aqueous continuous phase is all oil, a non-aqueous fluid, a water-in-oil emulsion, a water-in-non-aqueous emulsion, a brine-in-oil emulsion, or a brine-in-non-aqueous emulsion. In oil-based fluids, solid particles are suspended in a continuous phase consisting of oil or another non-aqueous fluid. Water or brine can be emulsified in the oil; therefore, the oil is the continuous phase. In oil-based fluids, the oil may consist of any oil or water-immiscible fluid that may include, but is not limited to, diesel, mineral oil, esters, refinery cuts and blends, or alpha-olefins. Oil-based fluid as defined herein may also include synthetic-based fluids or muds (SBMs), which are synthetically produced rather than refined from naturally-occurring materials. Synthetic-based fluids often include, but are not necessarily limited to, olefin oligomers of ethylene, esters made from vegetable fatty acids and alcohols, ethers and polyethers made from alcohols and polyalcohols, paraffinic, or aromatic, hydrocarbons alkyl benzenes, terpenes and other natural products and mixtures of these types.

There are a variety of functions and characteristics that are expected of completion fluids. The completion fluid may be placed in a well to facilitate final operations prior to initiation of production. Completion fluids are typically brines, such as chlorides, bromides, and/or formates, but may be any non-damaging fluid having proper density and flow characteristics. Suitable salts for forming the brines include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof. Chemical compatibility of the completion fluid with the reservoir formation and formation fluids is key. Chemical additives, such as polymers and surfactants are known in the art for being introduced to the brines used in well servicing fluids for various reasons that include, but are not limited to, increasing viscosity, and increasing the density of the brine. Completion fluids do not contain suspended solids.

Production fluid is the fluid that flows from a formation to the surface of an oil well. These fluids may include oil, gas, water, as well as any contaminants (e.g. $H_2S$, asphaltenes, etc.). The consistency and composition of the production fluid may vary.

Refinery fluids are fluids that may be further processed or refined at a refinery. A non-limiting example of a refinery process may include reducing or preventing the formation of foulants. Non-limiting examples of foulants may be or include hydrates, asphaltenes, coke, coke precursors, naphthenates, inorganic solid particles (e.g. sulfates, oxides, scale, and the like), and combinations thereof. Non-limiting examples of refinery fluids include crude oil, production water, and combinations thereof.

Servicing fluids, such as remediation fluids, stimulation fluids, workover fluids, and the like, have several functions and characteristics necessary for repairing a damaged well. Such fluids may be used for breaking emulsions already formed and for removing formation damage that may have occurred during the drilling, completion and/or production operations. The terms "remedial operations" and "remediate" are defined herein to include a lowering of the viscosity of gel damage and/or the partial or complete removal of damage of any type from a subterranean formation. Similarly, the term "remediation fluid" is defined herein to include any fluid that may be useful in remedial operations. A stimulation fluid may be a treatment fluid prepared to stimulate, restore, or enhance the productivity of a well, such as fracturing fluids and/or matrix stimulation fluids in one non-limiting example.

Hydraulic fracturing is a type of stimulation operation, which uses pump rate and hydraulic pressure to fracture or crack a subterranean formation in a process for improving the recovery of hydrocarbons from the formation. Once the crack or cracks are made, high permeability proppant relative to the formation permeability is pumped into the fracture to prop open the crack. When the applied pump rates and pressures are reduced or removed from the formation, the crack or fracture cannot close or heal completely because the high permeability proppant keeps the crack open. The propped crack or fracture provides a high permeability path connecting the producing wellbore to a larger formation area to enhance the production of hydrocarbons.

The development of suitable fracturing fluids is a complex art because the fluids must simultaneously meet a number of conditions. For example, they must be stable at high temperatures and/or high pump rates and shear rates that can cause the fluids to degrade and prematurely settle out the proppant before the fracturing operation is complete. Various fluids have been developed, but most commercially used fracturing fluids are aqueous based liquids that have either been gelled or foamed to better suspend the proppants within the fluid.

Injection fluids may be used in enhanced oil recovery (EOR) operations, which are sophisticated procedures that use viscous forces and/or interfacial forces to increase the hydrocarbon production, e.g. crude oil, from oil reservoirs. The EOR procedures may be initiated at any time after the primary productive life of an oil reservoir when the oil production begins to decline. The efficiency of EOR operations may depend on reservoir temperature, pressure, depth, net pay, permeability, residual oil and water saturations, porosity, fluid properties, such as oil API gravity and viscosity, and the like.

EOR operations are considered a secondary or tertiary method of hydrocarbon recovery and may be necessary when the primary and/or secondary recovery operation has left behind a substantial quantity of hydrocarbons in the subterranean formation. Primary methods of oil recovery use the natural energy of the reservoir to produce oil or gas and do not require external fluids or heat as a driving energy; EOR methods are used to inject materials into the reservoir that are not normally present in the reservoir.

Secondary EOR methods of oil recovery inject external fluids into the reservoir, such as water and/or gas, to re-pressurize the reservoir and increase the oil displacement. Tertiary EOR methods include the injection of special fluids, such as chemicals, miscible gases and/or thermal energy. The EOR operations follow the primary operations and target the interplay of capillary and viscous forces within the reservoir. For example, in EOR operations, the energy for producing the remaining hydrocarbons from the subterranean formation may be supplied by the injection of fluids into the formation under pressure through one or more injection wells penetrating the formation, whereby the injection fluids drive the hydrocarbons to one or more producing wells penetrating the formation. EOR operations are typically performed by injecting the fluid through the injection well into the subterranean reservoir to restore formation pressure, improve oil displacement or fluid flow in the reservoir, and the like.

Examples of EOR operations include water-based flooding and gas injection methods. Water-based flooding may also be termed 'chemical flooding' if chemicals are added to the water-based injection fluid. Water-based flooding may be or include, polymer flooding, ASP (alkali/surfactant/polymer) flooding, SP (surfactant/polymer) flooding, low salinity water and microbial EOR; gas injection includes immiscible and miscible gas methods, such as carbon dioxide flooding, and the like.

It would be desirable if additives were developed for fluid compositions used during hydrocarbon recovery to depress the freezing point of the fluid compositions.

SUMMARY

There is provided, in one form, an additive composition for a base fluid, such as but not limited to, a drilling fluid, a completion fluid, a production fluid, a servicing fluid, an injection fluid, a refinery fluid, and combinations thereof. The additive may have or include an antifreeze protein that is at least 75% homologous to the amino acid sequence of SEQ ID NO:2.

There is provided, in a non-limiting form, a fluid composition having a base fluid and an antifreeze protein that is at least 75% homologous to the amino acid sequence of SEQ ID NO:2. The base fluid may be or include, but is not limited to, drilling fluids, servicing fluids, production fluids, completion fluids, injection fluids, refinery fluids, and combinations thereof.

There is further provided in an alternative non-limiting embodiment of a method that may include circulating a fluid composition into a subterranean reservoir wellbore. The fluid composition may have or include at least one antifreeze protein that is at least 75% homologous to the amino acid sequence of SEQ ID NO:2 in an amount effective to depress the freezing point of the fluid composition.

The antifreeze protein appears to minimize the amount of hydrate formation in downhole fluids.

BRIEF DESCRIPTION OF THE DRAWINGS

In order to more fully understand the drawings referred to in the detailed description, a brief description of each drawing is presented here.

DETAILED DESCRIPTION

It has been discovered that an additive composition having an antifreeze protein derived from *Marinomonas primoryensis* may be added to a base fluid to depress the freezing point of the resulting fluid composition. Alternatively, the additive may decrease or minimize an amount of at least one substance within the fluid composition, such as but not limited to hydrate formation, scale, and combinations thereof. In addition to being biodegradable, the antifreeze proteins may be less toxic to the environment and may be made from renewable resources. The use of antifreeze proteins in a base fluid may provide a renewable alternative to conventional additives (non-biodegradable) that are used in downhole fluids to decrease hydrate formation, scale, and combinations thereof.

Although the inventors do not wish to be bound to a particular theory, it is thought that the antifreeze protein may function by one of two ways. One mechanism may be a short-range direct interaction between the surface of the antifreeze protein and the growing ice face, and the other mechanism may be a long-range interaction by protein-induced water dynamics. The dynamics may extend up to about 20 angstroms (about 7 hydration shells from the antifreeze protein) from the surface of the antifreeze protein. The antifreeze protein may reduce the ability of the water molecules to form a crystal matrix. In a non-limiting embodiment, the antifreeze protein may be used to reduce salt crystallization and/or may be used as an antifreeze/winterizing agent or within an antifreeze/winterizing additive. A 'hydration shell', also known as a solvation shell, is a shell of any chemical species that may act as a solvent by surrounding a solute species; here, the solvent may be water or another aqueous-base fluid.

'Derived from' with respect to the antifreeze protein is meant to include whole antifreeze proteins or antifreeze protein fragments, where the antifreeze protein originated from *M. primoryensis* bacterium and was isolated from that particular species; 'derived from' also encompasses polypeptides identical in amino acid sequence to the active site (e.g. the ice binding site in a non-limiting example) of the *M. primoryensis* bacterium that are recombinantly expressed in a host cell expression system or chemically synthesized. 'Recombinant DNA' is DNA that has been formed artificially by combining constituents from different organisms, such as inserting the antifreeze protein into an *E. coli* host cell for a cloned reproduction of the antifreeze protein in a non-limiting example.

'Derived from' also includes derivatives of the *M. primoryensis* antifreeze proteins, such as a polypeptide or fragment that may be substantially similar in primary structural sequence to an antifreeze protein described herein, but which may include chemical and/or biochemical modifications that are not found in the native polypeptide. Such modifications may be or include, but are not limited to a label, such as a radioactive isotope, a fluorophore, or an enzymatic label useful in tracing the antifreeze protein. The label or other modification may be useful in isolating the antifreeze protein from the *M. primoryensis* bacterium and/or other expression system (*E. coli* as described below). The label or other modification may be used to identify the antifreeze protein once the downhole fluid needs to be recovered from a subterranean reservoir wellbore and/or fluid composition. Other non-limiting modifications may be or include a formation of a salt bridge to impart additional stability to the antifreeze protein.

The primary structural sequence is the linear sequence of nucleotides that are linked together by phosphodiester bonds to form the primary structure of (deoxyribonucleic acid) DNA for the antifreeze protein. The secondary structure of the DNA refers to the base pairing interactions within a single molecule or set of interacting molecules, such as a beta-helix in the antifreeze protein. Tertiary structure refers to the three-dimensional structure of the antifreeze protein formed from the nucleotide sequence. Quaternary structure refers to the interaction between at least two tertiary structures. For example, the nucleotide sequence of the antifreeze protein is the primary structure (see FIG. 1A SEQ NO: 1); a beta-helix within the antifreeze protein is an example of a secondary structure; the three-dimensional structure of the antifreeze protein is the tertiary structure; the quaternary structure refers to the interaction between the antifreeze protein and at least one other tertiary structure.

Antifreeze proteins may depress the freezing point of water (in the presence of ice crystals) in a non-colligative manner by binding to the surface of nascent ice crystals. Antifreeze proteins have a variety of tertiary structures and often no common primary nucleotide sequence similarities or secondary structures (e.g. structural motifs). Antifreeze proteins from different species may bind to different faces of an ice crystal, and no single mechanism has been proposed to account for ice binding affinity and specificity.

Antifreeze proteins (also known as AFPs) are typically found in animals and bacteria that inhabit below-freezing temperatures. AFPs may bind to ice crystals and reduce, inhibit, and/or prevent further growth or recrystallization of the ice crystals that would otherwise be fatal to the organisms. The difference between the melting point and the altered/depressed freezing point created by the AFP is also known as thermal hysteresis, which may be measured with a nanoliter osmometer. Organisms differ in their values of thermal hysteresis. For example, the maximum level of thermal hysteresis by a fish AFP is approximately −1.5° C. (29.3° F.); insect antifreeze proteins may be 10-30 times more active than fish antifreeze proteins. The spruce budworm may resist freezing at temperatures as low as about −30° C.; the *Upis ceramboides* (an Alaskan beetle) may survive in a temperature as low as about −60° C. by relying on antifreeze proteins, as well as available xylomannan sugars.

'Antifreeze protein' (AFP) is defined herein to be the active site of the antifreeze protein, which may be or include the whole protein, an active fragment of the protein, a mimetic of the protein, and combinations thereof. 'Fragment' as used herein is meant to include any amino acid sequence shorter than the full-length antifreeze protein, but where the fragment maintains similar activity to the full-length antifreeze proteins. Fragments may include a single contiguous sequence identical to a portion of the antifreeze protein sequence. Alternatively, the fragment may have or include several different shorter segments where each segment is identical in amino acid sequence to a different portion of the amino acid sequence of the antifreeze protein, but linked via amino acids differing in sequence from the antifreeze protein. 'Mimetic' as used herein may include polypeptides, which may be recombinant, and peptidomimetics, as well as small organic molecules, which exhibit similar or enhanced thermal hysteresis activity as compared to the antifreeze proteins described herein.

The gene for the antifreeze protein may be codon optimized to increase the efficiency of its expression in *E. coli*. The nucleotide sequence of the antifreeze protein is set forth in FIG. 1A (SEQ ID NO:1). The nucleotide sequence includes the coding sequence for the antifreeze protein, a linker, and a polyhistadine tag.

Figure 1A:
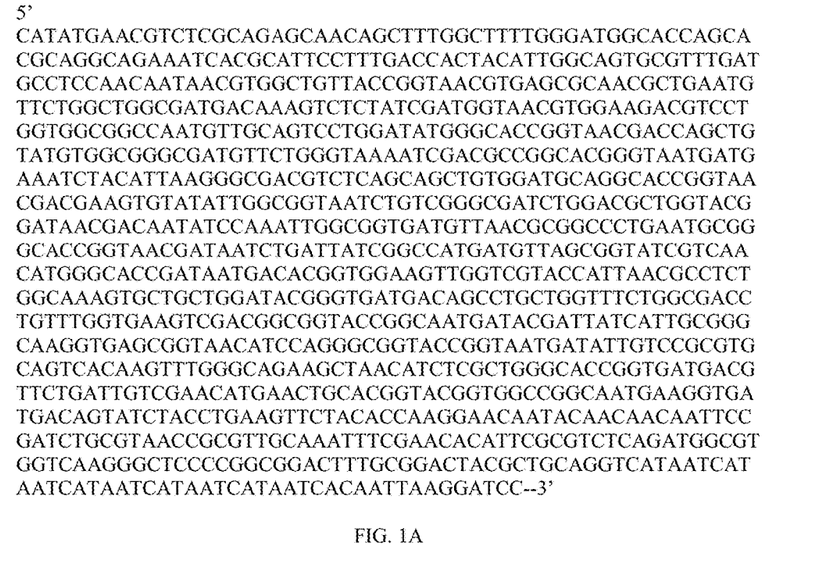
FIG. 1A (SEQ ID NO:1) represents the nucleotide sequence that codes for the antifreeze protein.

The gene coding for the antifreeze protein may have a nucleotide sequence that is substantially homologous to the nucleotide sequence of FIG. 1A (SEQ ID NO:1). The term "substantially homologous" is used herein to denote nucleotides having at least 75% sequence identity to the sequence shown in FIG. 1A (SEQ ID NO:1), alternatively from about 80% independently to about 99.5%, or from about 85% independently to about 95%. As used herein with respect to a range, "independently" means that any threshold may be used together with another threshold to give a suitable alternative range, e.g. about 75% independently to about 85% is also considered a suitable alternative range.

Figure 1B:
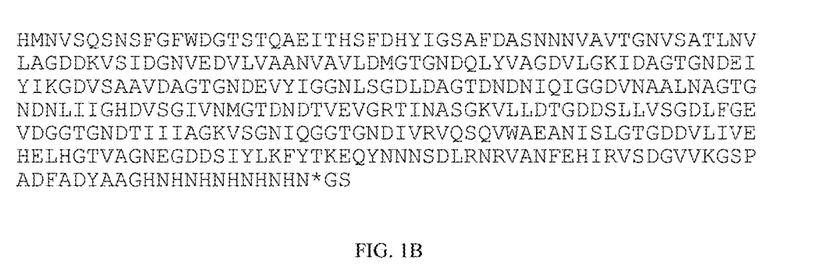
FIG. 1B (SEQ ID NO:2) represents the amino acid sequence of the antifreeze protein.

The translated amino acid sequence of the antifreeze protein is shown in FIG. 1B (SEQ ID NO:2). Typically, the translated amino acid sequence of the antifreeze protein may be used in the base fluid in a form that is at least 60% similar to the translated amino acid sequence set forth in FIG. 1B (SEQ ID NO:2), alternatively from about 75% independently to about 99.5%, or from about 85% independently to about 95% in another non-limiting embodiment. In a non-limiting embodiment, the isolated antifreeze protein is substantially free of other proteins. The antifreeze protein may be in a form that is at least 40% pure, alternatively from about 60% pure independently to about 99.5% pure, or from about 75% pure independently to about 90% pure as determined by SDS-PAGE.

The AFP may have or include a tag, and a linker. A linker is a self-complementary oligomer that contains a recognition sequence for a particular restriction enzyme. The restriction enzyme may cleave the linker from the DNA and generate 'sticky ends' prior to cloning the antifreeze protein. In a non-limiting embodiment, the linker may be hydrophobic or hydrophilic. Depending on the temperature, pressure, or other conditions of the base fluid, the linker may be hydrophobic. In a non-limiting embodiment, the linker may be aspartic acid, tyrosine, alanine, alanine, glycine (DYAAG) as depicted in FIG. 1B. Alternatively, the linker may be aspartic acid, alanine, valine, isoleucine, aspartic acid (DAVID) or another 5 sequence amino acid sequence.

The tag may be a polyhistidine tag (also known as a 'His-tag', hexahistadine tag, 6×His-tag, His6-tag, and the like) attached to the C-terminal end of the AFP in a non-limiting embodiment. A polyhistidine tag is an amino acid motif that may be attached to a protein, which has at least six histidine (His) residues. The polyhistadine tag may be depicted in FIG. 1B as being at the C-terminus end, but the polyhistadine tag may be at the N-terminus and/or the C-terminus. Polyhistadine-tags may be used for affinity purification of a polyhistadine-tagged recombinant protein expressed in *E. coli* and/or other prokaryotic expression systems.

In a non-limiting embodiment, the polyhistadine-tag may contribute to scale inhibition properties of the antifreeze protein. Although the inventors do not wish to be bound to a particular theory, it is believed that the polyhistadine tag may have a strong affinity for divalent cations, so the polyhistadine tage may chelate $Ba^{2+}$ or $Ca^{2+}$ in solution. Additionally, the carboxyl chemistry on the surface of the antifreeze protein may chelate $Ba^{2+}$ or $Ca^{2+}$ in solution. Alternatively, because of the polyhistidine-tag's affinity for metal compounds, the polyhistadine tag may attach or cluster on solid surfaces (e.g. pipes), thereby attaching the AFP to the solid surfaces, to further reduce or prevent freezing on the interior pipe surface.

A non-limiting example of the antifreeze protein may be or include but is not limited to MpAFP_RIV, which is a recombinant antifreeze protein derived from *M. primoryensis*. The active fragment and/or ice-binding site may fold as a right-handed $Ca^{2+}$-bound parallel beta-helix roughly 70 angstroms long and 20×10 angstroms in cross-section. The AFP may have a 34-kDa domain, and it may fold as a $Ca^{2+}$-bound parallel beta-helix with an extensive array of ice-like surface waters that are anchored via hydrogen bonds directly to the polypeptide backbone and adjacent side chains.

Each β-helix may have a first side and a second side. The first side of the β-helix may have a single row of $Ca^{+2}$ ions, and the second side may have a hydrophobic core. Every coil of the beta-helix, about 19 amino acids in length, may have one 6-residue $Ca^{2+}$ binding turn and three short beta strands separated by Glycine-rich turns. The antifreeze protein may be dependent on $Ca^{2+}$ for thermal hysteresis, and this activity may be resistant to proteolysis by trypsin only if $Ca^{2+}$ is present, which suggests a structural role for the cation as opposed to a cofactor role seen in some antifreeze proteins found in Atlantic herring fish.

The ice binding site (IBS) of the *M. primoryensis* AFP may have a long and flat IBS that runs the length of its $Ca^{2+}$ bound side having a threonine and aspartic acid (or aspartate) residues that project outward from the $Ca^{2+}$ binding turns in a non-limiting embodiment. A glycine may separate threonine and aspartic acid (or aspartate) in each turn, and this pattern may maintain the IBS's flatness and regularity. The IBS may arrange water molecules into a specific ice-like lattice where the ice-like water molecules may enclose the gamma-methyl of each threonine, and the cage may be anchored to the IBS by hydrogen bonds to the main-chain nitrogen and side-chain hydroxyl of each threonine. Waters may also be hydrogen-bonded to the main-chain nitrogen of each Glycine and side-chain oxygen of each aspartic acid (aspartate). Microscopic ice crystals may form in the presence of the AFP as hexagonal plates; thus, the AFP may have an affinity toward the basal and primary prism planes of ice/water crystals in a non-limiting embodiment. In a non-limiting embodiment, the AFP may partially form the ligand before binding to it. More information related to the tertiary structure of the antifreeze protein and ice-binding site may be found in "*Anchored Clathrate Waters Bind Antifreeze Proteins to Ice*", Garnham, et. al., vol. 108 no. 18, May 2011; which is herein incorporated by reference in its entirety.

The antifreeze protein may be considered a hyperactive antifreeze protein when compared to other AFPs. For example, the *M. primoryensis* antifreeze protein may have a thermal hysteresis level of just under 2° C. at a concentration of 0.1 mg/mL; whereas a typical fish AFP may only produce about a 0.1° C. of thermal hysteresis. A hyperactive AFP, such as the antifreeze protein derived from *M. primoryensis*, may have a thermal hysteresis level of at least about 5 times greater than a fish AFP, alternatively from about 3 times greater than a fish AFP independently to as much as about 15 times greater. More information related to the thermal hysteresis of MpAFP_RIV may be found in "*A Ca2+-dependent Bacterial Antifreeze Protein Domain Has a Novel b-Helical Ice-Binding Fold*", Garnham et al., Biochemical Journal (2008), 411, 171-180.

To obtain the AFP, the *M. primoryensis* bacterium may be plated on a growth medium, such as an agar, which is conducive to the growth of the *M. primoryensis* bacterium in a non-limiting embodiment. The AFP may be directly isolated from the *M. primoryensis* to be added to or used within a fluid composition for depressing the freezing point of the base fluid, reducing/decreasing hydrate formation, reducing/decreasing scale formation, and combinations thereof. 'Isolated' is defined herein to denote that the antifreeze protein has been removed from the intact cells or cellular debris, and is in a condition other than its native environment, is free of other extraneous or unwanted nucleic acids, proteases, and lipids, in a form suitable for use as an antifreeze protein as described herein.

In a non-limiting embodiment, the antifreeze protein of the *M. primoryensis* bacterium may be inserted into or joined to a vector for insertion into a plasmid. A vector is a DNA molecule that may be used as a vehicle to artificially carry genetic material from a foreign cell and/or organism. A plasmid is defined as a circular extrachromosomal element found naturally in bacteria and some other organisms, which may be genetically engineered to clone DNA fragments. The plasmid may then be inserted into a host bacterium cell, such as *Escherichia coli*, where the host cell may replicate and/or express the foreign DNA. The *E. coli* cells may be plated on a growth medium, such as an agar, which is conducive to the growth of *E. coli*. The growth of *E. coli* propagates the AFP as clones within each *E. coli* cell. The AFP may be isolated from the *E. coli* cells and added to or used within a fluid composition. A non-limiting expression vector having the AFP of the protein may be a commercially available pET-11a expression vector, which is supplied by Agilent.

Figure 2:
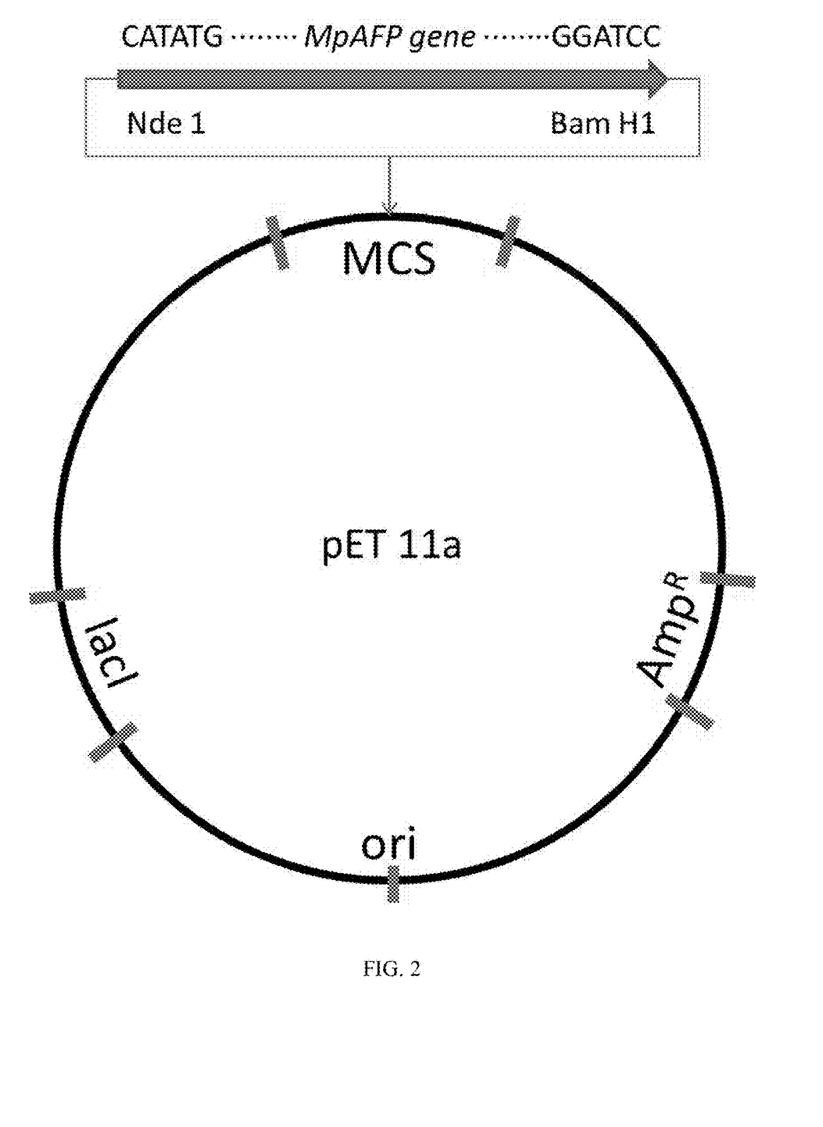
FIG. 2 represents the creation of the plasmid pET11a-MpAFP having the antifreeze protein.

FIG. 2 is a depiction of the created plasmid pET11a-MpAFP after cloning the antifreeze protein thereinto. The multiple cloning site (MCS) is a short segment of DNA that has several restriction sites, such as Nde1 and BamH1 depicted here in a non-limiting embodiment. Nde1 is a type II restriction enzyme that may cut open specific sequence targets; specifically, Nde1 may be used to cut open the reading frames in the plasmid to insert the antifreeze protein genes. BamHI is also a type II restriction endonuclease that recognizes the sequence 5'-GGATCC-3', and cleaves these sequences just after the 5'-guanine on each strand to leave sticky ends that are 4 b.p. long.

$Amp^R$ regulates the expression of β-lactamase, ori is the DNA sequence that signals for the origin of replication (also known as 'origin'). lacI codes for the lactose repressor.

To isolate or obtain the AFP from *E. coli*, the *E. coli* cells may be harvested via centrifugation to produce a cell pellet. The cell pellet may be lysed either by physical means or by chemical means, such as detergents and/or enzymes (e.g. lysozyme) to produce a lysate. The raw lysate may contain the recombinant protein, as well as other proteins originating from the bacterial host. Thus, the raw lysate mixture may be incubated with an affinity resin having bound bivalent nickel and/or cobalt ions. The affinity resin may be sepharose/agarose functionalised with a chelator, such as but not limited to iminodiacetic acid (Ni-IDA), nitrilotriacetic acid (Ni-NTA), carboxylmethylaspartate (Co-CMA), and combinations thereof. The polyhistadine-tag may bind to the affinity resin with micromolar affinity. The affinity resin with the attached polyhistadine-tag(s) may then be washed with a phosphate buffer to remove the proteins that do not bind thereto, while the AFP remains attached to the affinity resin via the polyhistadine tag. Thus, a polyhistadine tag allows the AFP to be purified in this manner. SDS-PAGE, Western blotting, and the like may be used to further assess the purity and amount of purified antifreeze protein.

The AFP may be in a powder form and/or a liquid form (e.g. in solution) when added to or included in the fluid composition. The AFP may be part of an additive where the additive includes the AFP, as well as other components to aid the antifreeze protein in depressing the freezing point, minimizing hydrate formation, and minimizing scale formation of the fluid composition.

The AFP or additive may be added or present in the fluid composition in an amount ranging from about 0.01 vol % independently to about 10 vol % of the total base fluid, alternatively from about 0.1 vol % independently to about 5 vol %, or from about 0.25 vol % independently to about 3 vol %. Alternatively, the AFP may be present within the additive composition in an amount ranging from about 1 ppm to about 10 ppt as compared to the total base fluid. The AFP may depress the freezing point of the fluid composition by at least 0.5° C., alternatively from about 1° C. independently to about 30° C., alternatively from about 5° C. independently to about 20° C., or from about 10° C. independently to about 15° C.

The additive composition may also include a winterizing agent, a kinetic hydrate Inhibitor, a pour point depressant, an anti-agglomerant, common fracturing fluid additives, and combinations thereof. The winterizing agent may be or include, but is not limited to, alcohols, glycols, diols, or glycol ethers including those that generally contain a hydroxyl group or multiple hydroxyl groups. Such alcohols, glycols, diols, or glycol ethers may be selected from, in non-limiting embodiments, methanol, ethanol, propanol, isopropanol, butanol, ethylene glycol, propylene glycol, butylene glycol, hexylene glycol, diethylene glycol, dipropylene glycol, triethylene glycol, tripropylene glycol, propylene glycol methyl ether, dipropylene glycol methyl ether, tripropylene glycol methyl ether, propylene glycol propyl ether, dipropylene glycol propyl ether, tripropylene glycol propyl ether, propylene glycol butyl ether, dipropylene glycol butyl ether, tripropylene glycol butyl ether, propylene glycol phenyl ether, dipropylene glycol dimethyl ether, diethylene glycol ethyl ether, diethylene glycol methyl ether, diethylene glycol butyl ether, diethylene glycol hexyl ether, ethylene glycol propyl ether, ethylene glycol butyl ether, ethylene glycol hexyl ether, triethylene glycol methyl ether, triethylene glycol ethyl ether, triethylene glycol butyl ether, ethylene glycol phenyl ether, ethylene glycol ethyl ether, polyethylene glycol, monosaccharide, polypropylene glycol, dimethyl sulfoxide, glycerol, glycerine, copolymers thereof, and combinations thereof.

Once the AFP (or an additive that includes the AFP) is added to the base fluid, the resulting fluid composition may be used in a downhole operation. The base fluid may be or include, but is not limited to a drilling fluid, a completion fluid, a servicing fluid (e.g. fracturing fluid), an injection fluid, a production fluid, a refinery fluid, and combinations thereof. In a non-limiting embodiment, the base fluid may be an aqueous fluid, a non-aqueous fluid, and combinations thereof. In another non-limiting embodiment, the base fluid or fluid composition may be contained in an oil pipeline, gas pipeline, a refinery (e.g. separation vessels, dehydration units, gas lines, and pipelines), and combinations thereof.

In a non-limiting embodiment, the fluid composition may be circulated into a subterranean reservoir wellbore, and the fluid composition may have or include an effective amount of at least one antifreeze protein to depress the freezing point of the fluid composition relative to the melting point. The method may further include decreasing the amount of at least one substance within the fluid composition, such as but not limited to hydrate formation, scale, and combinations thereof. Parameters that may be used to assess the effectiveness of hydrate inhibitors may include measurement of hydrate formation kinetics (rate of gas uptake), driving force measurements (e.g. the degree of sub-cooling required to initiate hydrate formation), and induction time. Methods for measuring these parameters may be used to assess the ability of the antifreeze protein to reduce or inhibit hydrate formation. 'Effective amount' is defined herein to mean any amount of antifreeze protein that may depress the freezing temperature of the fluid composition; alternatively, 'effective amount' is defined herein to mean any amount of the antifreeze protein that may decrease the amount of scale, hydrates, and combinations thereof.

Determination of the induction time for hydrate formation in the presence or absence of antifreeze proteins may be used as an assay for the inhibition activity of the antifreeze protein. Induction time may be the time required for the onset point of the crystallization. In this assay, samples may be kept at constant temperature with constant stirring and a sudden rise of temperature signals the onset point of crystallization of hydrates. The effect of a number of parameters including concentration of the antifreeze protein, temperature, gas, and salt are determined and data subject to statistical analysis. Freezing points may be obtained with differential scanning calorimetry (DSC) as a measure of inhibition activity and for comparison with known kinetic inhibitors.

The growth rate of hydrates in the presence of the antifreeze protein may also be determined and compared to activities of other antifreeze proteins and/or known kinetic inhibitors. Experiments may be performed by capturing images of the hydrate crystals growing in solution, using a specially built crystal-growth-observation apparatus. Effects of concentration of the antifreeze protein, temperature, gas, and salt on the growth rate may also be examined.

In the foregoing specification, the invention has been described with reference to specific embodiments thereof, and has been described as effective in providing methods, additive compositions, and fluid compositions for depressing the freezing point of a base fluid, reducing/minimizing the amount of hydrates within the base fluid, reducing/minimizing the amount of scale in the base fluid, and combinations thereof. However, it will be evident that various modifications and changes can be made thereto without departing from the broader spirit or scope of the invention as set forth in the appended claims. Accordingly, the specification is to be regarded in an illustrative rather than a restrictive sense. For example, specific base fluids, amino acids, additives, winterizing agents, kinetic hydrate Inhibitors, pour point depressants, anti-agglomerants, and the like falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the additive composition for a base fluid, such as a drilling fluid, a completion fluid, a production fluid, a servicing fluid, an injection fluid, a refinery fluid, and combinations thereof may consist of or consist essentially an antifreeze protein that is at least 75% homologous to the amino acid sequence of SEQ ID NO:2.

The fluid composition may consist of or consist essentially of a base fluid and an antifreeze protein that is at least 75% homologous to the amino acid sequence of SEQ ID NO:2; the base fluid may be or include, but is not limited to a drilling fluid, a completion fluid, a production fluid, a servicing fluid, an injection fluid, a refinery fluid, and combinations thereof.

The method may consist of or consist essentially of circulating a fluid composition into a subterranean reservoir wellbore; the fluid composition may have or include at least one antifreeze protein that is at least 75% homologous to the amino acid sequence of SEQ ID NO:2 in an effective amount to depress the freezing point of the fluid composition.

The words "comprising" and "comprises" as used throughout the claims, are to be interpreted to mean "including but not limited to" and "includes but not limited to", respectively.

What is claimed is:

1. An additive composition for a base fluid selected from the group consisting of a drilling fluid, a completion fluid, a production fluid, a servicing fluid, an injection fluid, a refinery fluid, and combinations thereof; wherein the additive comprises an antifreeze protein that is at least 75% homologous to the amino acid sequence of SEQ ID NO:2, and wherein the antifreeze protein comprises a polyhistadine tag attached to a C-terminal end of the antifreeze protein.

2. The additive composition of claim 1, wherein the amount of the antifreeze protein within the additive composition ranges from about 1 ppm to about 10 ppt as compared to the total base fluid.

3. The additive composition of claim 1, further comprising an additive selected from the group consisting of a winterizing agent, a kinetic hydrate Inhibitor, a pour point depressant, an anti-agglomerant, a fracturing fluid additive, and combinations thereof.

4. The additive composition of claim 3, wherein the winterizing agent is selected from the group consisting of methanol, ethanol, propanol, isopropanol, butanol, ethylene glycol, propylene glycol, butylene glycol, hexylene glycol, diethylene glycol, dipropylene glycol, triethylene glycol, tripropylene glycol, propylene glycol methyl ether, dipropylene glycol methyl ether, tripropylene glycol methyl ether, propylene glycol propyl ether, dipropylene glycol propyl ether, tripropylene glycol propyl ether, propylene glycol butyl ether, dipropylene glycol butyl ether, tripropylene glycol butyl ether, propylene glycol phenyl ether, dipropylene glycol dimethyl ether, diethylene glycol ethyl ether, diethylene glycol methyl ether, diethylene glycol butyl ether, diethylene glycol hexyl ether, ethylene glycol propyl ether, ethylene glycol butyl ether, ethylene glycol hexyl ether, triethylene glycol methyl ether, triethylene glycol ethyl ether, triethylene glycol butyl ether, ethylene glycol phenyl ether, ethylene glycol ethyl ether, polyethylene glycol, monosaccharide, polypropylene glycol, dimethyl sulfoxide, glycerol, glycerine, copolymers thereof, and combinations thereof.

5. A fluid composition comprises:
a base fluid selected from the group consisting of drilling fluids, servicing fluids, production fluids, completion fluids, injection fluids, refinery fluids, and combinations thereof; and
an antifreeze protein that is at least 75% homologous to the amino acid sequence of SEQ ID NO:2, and wherein the antifreeze protein comprises a polyhistadine tag attached to a C-terminal end of the antifreeze protein.

6. The fluid composition of claim 5, wherein the amount of the antifreeze protein within the additive composition ranges from about 1 ppm to about 10 ppt as compared to the total base fluid.

7. The fluid composition of claim 5, wherein the fluid composition further comprises an additive selected from the group consisting of a winterizing agent, a kinetic hydrate Inhibitor, a pour point depressant, an anti-agglomerant, a fracturing fluid additive, and combinations thereof.

8. The fluid composition of claim 7, wherein the winterizing agent is selected from the group consisting of methanol, ethanol, propanol, isopropanol, butanol, ethylene glycol, propylene glycol, butylene glycol, hexylene glycol, diethylene glycol, dipropylene glycol, triethylene glycol, tripropylene glycol, propylene glycol methyl ether, dipropylene glycol methyl ether, tripropylene glycol methyl ether, propylene glycol propyl ether, dipropylene glycol propyl ether, tripropylene glycol propyl ether, propylene glycol butyl ether, dipropylene glycol butyl ether, tripropylene glycol butyl ether, propylene glycol phenyl ether, dipropylene glycol dimethyl ether, diethylene glycol ethyl ether, diethylene glycol methyl ether, diethylene glycol butyl ether, diethylene glycol hexyl ether, ethylene glycol propyl ether, ethylene glycol butyl ether, ethylene glycol hexyl ether, triethylene glycol methyl ether, triethylene glycol ethyl ether, triethylene glycol butyl ether, ethylene glycol phenyl ether, ethylene glycol ethyl ether, polyethylene glycol, monosaccharide, polypropylene glycol, dimethyl sulfoxide, glycerol, glycerine, copolymers thereof, and combinations thereof.

9. The fluid composition of claim 5, wherein the fluid composition further comprises a substance selected from the group consisting of hydrates, scale, and combinations thereof; and wherein the fluid composition comprises the substance in a reduced amount as compared to an identical fluid composition absent the antifreeze protein.

* * * * *

SEQUENCE LISTING

```
<160> NUMBER OF SEQ ID NOS: 2

<210> SEQ ID NO 1
<211> LENGTH: 1026
<212> TYPE: DNA
<213> ORGANISM: Marinonomas primoryensis

<400> SEQUENCE: 1
catatgaacg tctcgcagag caacagcttt ggcttttggg atggcaccag cacgcaggca      60
gaaatcacgc attcctttga ccactacatt ggcagtgcgt ttgatgcctc caacaataac     120
gtggctgtta ccggtaacgt gagcgcaacg ctgaatgttc tggctggcga tgacaaagtc     180
tctatcgatg gtaacgtgga agacgtcctg gtggcggcca atgttgcagt cctggatatg     240
ggcaccggta acgaccagct gtatgtggcg ggcgatgttc tgggtaaaat cgacgccggc     300
acgggtaatg atgaaatcta cattaagggc gacgtctcag cagctgtgga tgcaggcacc     360
```

```
ggtaacgacg aagtgtatat tggcggtaat ctgtcgggcg atctggacgc tggtacggat    420
aacgacaata tccaaattgg cggtgatgtt aacgcggccc tgaatgcggg caccggtaac    480
gataatctga ttatcggcca tgatgttagc ggtatcgtca acatgggcac cgataatgac    540
acggtggaag ttggtcgtac cattaacgcc tctggcaaag tgctgctgga tacgggtgat    600
gacagcctgc tggtttctgg cgacctgttt ggtgaagtcg acggcggtac cggcaatgat    660
acgattatca ttgcgggcaa ggtgagcggt aacatccagg gcggtaccgg taatgatatt    720
gtccgcgtgc agtcacaagt ttgggcagaa gctaacatct cgctgggcac cggtgatgac    780
gttctgattg tcgaacatga actgcacggt acggtggccg gcaatgaagg tgatgacagt    840
atctacctga agttctacac caaggaacaa tacaacaaca attccgatct gcgtaaccgc    900
gttgcaaatt tcgaacacat tcgcgtctca gatggcgtgg tcaagggctc cccggcggac    960
tttgcggact acgctgcagg tcataatcat aatcataatc ataatcataa tcacaattaa   1020
ggatcc                                                              1026
```

```
<210> SEQ ID NO 2
<211> LENGTH: 341
<212> TYPE: PRT
<213> ORGANISM: Marinomonas primoryensis

<400> SEQUENCE: 2

His Met Asn Val Ser Gln Ser Asn Ser Phe Gly Phe Trp Asp Gly Thr
1               5                   10                  15

Ser Thr Gln Ala Glu Ile Thr His Ser Phe Asp His Tyr Ile Gly Ser
            20                  25                  30

Ala Phe Asp Ala Ser Asn Asn Val Ala Val Thr Gly Asn Val Ser
        35                  40                  45

Ala Thr Leu Asn Val Leu Ala Gly Asp Asp Lys Val Ser Ile Asp Gly
    50                  55                  60

Asn Val Glu Asp Val Leu Val Ala Ala Asn Val Ala Val Leu Asp Met
65                  70                  75                  80

Gly Thr Gly Asn Asp Gln Leu Tyr Val Ala Gly Asp Val Leu Gly Lys
                85                  90                  95

Ile Asp Ala Gly Thr Gly Asn Asp Glu Ile Tyr Ile Lys Gly Asp Val
            100                 105                 110

Ser Ala Ala Val Asp Ala Gly Thr Gly Asn Asp Glu Val Tyr Ile Gly
        115                 120                 125

Gly Asn Leu Ser Gly Asp Leu Asp Ala Gly Thr Asp Asn Asp Asn Ile
    130                 135                 140

Gln Ile Gly Gly Asp Val Asn Ala Ala Leu Asn Ala Gly Thr Gly Asn
145                 150                 155                 160

Asp Asn Leu Ile Ile Gly His Asp Val Ser Gly Ile Val Asn Met Gly
                165                 170                 175

Thr Asp Asn Asp Thr Val Glu Val Gly Arg Thr Ile Asn Ala Ser Gly
            180                 185                 190

Lys Val Leu Leu Asp Thr Gly Asp Asp Ser Leu Leu Val Ser Gly Asp
        195                 200                 205

Leu Phe Gly Glu Val Asp Gly Gly Thr Gly Asn Asp Thr Ile Ile Ile
    210                 215                 220

Ala Gly Lys Val Ser Gly Asn Ile Gln Gly Gly Thr Gly Asn Asp Ile
225                 230                 235                 240

Val Arg Val Gln Ser Gln Val Trp Ala Glu Ala Asn Ile Ser Leu Gly
                245                 250                 255
```

```
Thr Gly Asp Asp Val Leu Ile Val Glu His Glu Leu His Gly Thr Val
            260                 265                 270

Ala Gly Asn Glu Gly Asp Asp Ser Ile Tyr Leu Lys Phe Tyr Thr Lys
        275                 280                 285

Glu Gln Tyr Asn Asn Asn Ser Asp Leu Arg Asn Arg Val Ala Asn Phe
    290                 295                 300

Glu His Ile Arg Val Ser Asp Gly Val Val Lys Gly Ser Pro Ala Asp
305             310                 315                 320

Phe Ala Asp Tyr Ala Ala Gly His Asn His Asn His Asn His Asn His
                325                 330                 335

Asn His Asn Gly Ser
            340
```